United States Patent [19]
Shead

[11] Patent Number: 5,773,714
[45] Date of Patent: Jun. 30, 1998

[54] SCANNER BEAM DYNAMIC DEFLECTION MEASUREMENT SYSTEM AND METHOD

[75] Inventor: Raymond P. Shead, Berkshire, England

[73] Assignee: Honeywell-Measurex Corporation, Cupertino, Calif.

[21] Appl. No.: 804,029

[22] Filed: Feb. 19, 1997

[51] Int. Cl.[6] .......................... G01N 21/86; G01N 37/00
[52] U.S. Cl. ........................ 73/105; 73/1.79; 73/1.81; 356/381; 356/382; 364/563; 364/568
[58] Field of Search .......................... 73/1.79, 1.81, 73/1.89, 105, 159; 356/379, 380, 381, 382, 383, 384, 385, 386, 387; 364/560, 562, 563, 564, 568, 571.01, 571.02, 571.03, 571.05; 250/252.1, 341.1, 339.04, 359.1; 324/206, 207.11, 207.12, 225, 226, 229

[56] References Cited

U.S. PATENT DOCUMENTS

| | | | |
|---|---|---|---|
| 3,306,103 | 2/1967 | Davis | 73/159 |
| 3,348,046 | 10/1967 | Lloyd . | |
| 3,621,259 | 11/1971 | Boissevain | 250/83.3 D |
| 4,276,480 | 6/1981 | Watson | 250/560 |
| 4,674,325 | 6/1987 | Kiyobe et al. | 324/630 |
| 4,678,915 | 7/1987 | Dahlquist et al. | 250/358.1 |
| 4,823,590 | 4/1989 | Kniest et al. | 73/1.81 |
| 4,955,225 | 9/1990 | Kniest et al. | 73/1.81 X |
| 5,117,093 | 5/1992 | Boissevain | 219/494 |
| 5,165,277 | 11/1992 | Bossen et al. | 73/159 |
| 5,210,593 | 5/1993 | Kramer | 356/381 |
| 5,569,835 | 10/1996 | Kenney et al. | 73/1.81 |

*Primary Examiner*—Hezron E. Williams
*Assistant Examiner*—Daniel S. Larkin
*Attorney, Agent, or Firm*—Loeb & Loeb LLP

[57] ABSTRACT

In a scanner used in a paper-making process to measure basis weight and other parameters of the fabricated paper sheet, variations in the separation of an opposed pair of sensing heads due to temperature induced deflections of upper and lower beams on which the heads are movably mounted as well as deflections and/or expansions of other portions of the support structure for the sensor are dynamically measured and compensated for. Temperature sensors mounted on carriages for the sensing heads measure the temperatures at different locations within the sensor support structure so that temperature differentials can be determined. The temperature differentials, which provide a measure of beam deflection at any given position of the head carrying carriage, are applied in accordance with a linearizing algorithm to correct the values provided by the sensing heads. A plurality of temperature sensors mounted on each carriage provide temperature differences between upper and lower portions and between opposite side portions of an associated beam so that beam deflection in both the vertical or Z direction and the lateral or X direction can be compensated for. Temperature sensors are also located on opposite faces of end support plates which support the upper and lower beams, to provide a measure of temperature induced deflection and/or relative expansion of the end support plates.

23 Claims, 5 Drawing Sheets

SCANNER BEAM DYNAMIC DEFLECTION MEASUREMENT SYSTEM AND METHOD

BACKGROUND OF THE INVENTION

1. Field of the Invention

The present invention relates to scanners used to measure basis weight and other parameters of paper or other sheet material during fabrication thereof, and more particularly to systems for measuring and compensating for thermal deflections in the scanner beam structure.

2. History of the Prior Art

In a typical process for fabricating sheet material such as paper, the formed sheet material is passed through a gauging apparatus or scanner prior to being wound onto a reel. In the case of paper, the scanner can measure different parameters such as moisture content, thickness or caliper, basis weight, gloss, color, and so forth.

In a typical scanner, gauging head assemblies disposed on opposite sides of the traveling paper sheet move in unison and in reciprocating fashion across the width of the paper so as to continuously scan different portions of the advancing paper. Usually, one of the heads carries a source of radiation which passes through the paper and is intercepted by a detector carried by the other head. In principle, the detected radiation can provide a precise measurement of paper parameters such as basis weight.

In scanners of the type described, the reciprocating motion of the opposite heads is typically accomplished by mounting the heads on carriages which traverse upper and lower horizontal beams of the scanner. In one type of scanner construction, the upper and lower beams are mounted on vertical, reinforced end support plates. Ideally, the upper and lower beams are perfectly straight so that the gap separating the upper and lower heads, and hence the radiation source and detector, remains constant as the heads traverse the width of the advancing paper sheet. As a practical matter, however, some deflection of the beams almost always occurs, due principally to temperature differences within the scanner support structure. Typically, the newly formed paper sheet is still hot, and radiant heat from the paper heats different parts of the support structure by different amounts. The resulting temperature gradients are major causes of beam distortion or deflection. When the upper and lower beams are thermally distorted, the separation between the heads varies as the heads traverse the width of the sheet. The resulting variations in the air gaps between the opposite heads and the adjacent surfaces of the paper sheet introduce measurement errors which can become particularly important in the case of very thin paper such as tissue where the mass of the air in the gaps on both sides of the paper sheet forms a significant portion of the total mass of the material in the radiation path between the source and detector. Besides such vertical or Z axis errors, measurement errors can also be introduced by X axis (machine direction) and/or Y axis (cross direction) misalignments between the radiation source and detector; these misalignments also can result from thermal distortion of the scanner support structure.

Over the years, workers in the art have used various approaches to solving the problem of scanner structure thermal distortion. One approach, involving the use of massive beams, attempts to prevent the beams from thermally distorting in the first place. Conventional scanner beams also have been reinforced in an effort to prevent thermal distortion. These approaches have generally proved unsuccessful. No matter how massive and/or rigid the beams were made, there was always some thermal distortion of the scanner support structure. Another approach involved attempts to maintain the temperature differences between various portions of the beams as close to zero as possible. As exemplified by U.S. Pat. No. 5,165,277, coolant is circulated through hollow beams. Another approach, exemplified by U.S. Pat. No. 3,621,259, has been to direct cooling air along the beams. None of these approaches have proven to be completely effective.

Because some beam deflection or distortion appears to be unavoidable, another approach has been to mechanically or thermally compensate for the distortion. A mechanical approach, exemplified by U.S. Pat. No. 3,348,046, adjusts the ways or tracks of the head carriages in an effort to assure parallelism thereof. In a thermal approach, exemplified by U.S. Pat. No. 5,117,093, the measured beam deflection is used to heat or cool the beams in an effort to induce counteracting deflections.

A further approach to the problem of beam deflection is to allow the beams to distort, measure the distortion and correct the gauge output accordingly. One technique is to store values representing the deflection and to use these values to correct the output of the gauge detector circuit. In an electromechanical version of this approach, as exemplified by U.S. Pat. No. 3,306,103, cam elements on a rotatable disk are adjusted in accordance with beam deflection. A cam follower controls a variable resistor in the sensor measurement circuit. In an electronic or software approach, a static profile correction array is stored in a memory and is used to apply corrections to the gauge output. The array is developed by attaching a sample of known basis weight to the sensor, and scanning without the presence of the paper sheet. The measured basis weight is compared to the known weight of the sample, and the error at each location across the scan is stored in a profile correction array to be used later to correct the scanner readings. This technique works only so long as the errors at the various locations do not change.

In a continuing effort to develop improved beam deflection measurement systems, dynamic measurement systems which measure deflection on-the-go or in real time have been developed. Such systems measure Z axis deflection (the vertical direction between the opposite heads) in dynamic fashion. An indirect dynamic gap measurement and correction approach is exemplified by U.S. Pat. No. 4,276,480, in which the head-to-head gap is measured optically using external position references. In U.S. Pat. No. 4,678,915, the head-to-head gap is measured directly through the paper using an inductive proximity or eddy current sensor. The resulting gap measurement is used to correct the uncorrected measured values according to variations in the separation of the heads. Error correction is continuously updated so that errors caused by variations in head gap are corrected on-the-go.

While the techniques for compensating for beam deflection disclosed in U.S. Pat. No. 4,678,915 have proven to be effective, nevertheless, there is a continuing need for alternative approaches that can effectively measure and correct not only for Z axis deflections, but deflections along the other axes as well, and that can do so on a substantially real time basis.

BRIEF DESCRIPTION OF THE INVENTION

Briefly stated, the present invention provides improved systems and methods for detecting and correcting for structural deflections due to temperature gradients in a sheet-gauging scanner. More particularly, the invention provides improved systems and methods for detecting and correcting for such deflections dynamically, in substantially real time.

In systems and methods according to the invention, temperature sensors, such as infrared surface temperature sensors, are placed at different locations relative to the support structure of a sheet-gauging scanner to measure the local temperatures at such locations. From the measured temperatures, temperature differences across structural members are determined. The temperature differences, which are related to the deflections of the structural members, are used to correct the output of the gauging apparatus, such as a basis weight sensor, for variations in output resulting from the thermally induced deflections. For example, the temperature sensors may be located so that temperature differences between upper and lower portions of each horizontal scanner beam can be determined, thereby providing a representation of beam deflections due to thermal effects in the vertical or Z axis direction. In addition, the sensors may be placed so as to provide temperature differences between opposite faces of each scanner beam, thereby providing a representation of beam deflection along the X axis or machine direction. Temperature sensors may also be placed on the opposite faces of the vertical end plates which support the upper and lower horizontal beams, so that deflection of the vertical end supports in the Y or cross direction can be measured and used additionally to correct sensing gauge measurement errors due to such deflections.

Dynamic measurement and correction for Z axis and X axis beam deflections are accomplished by mounting the temperature sensors so as to move with the reciprocating gauging heads. This may be accomplished by mounting the temperature sensors on the movable carriages on which the heads are mounted. A plurality of temperature sensors mounted on each carriage may include sensors positioned to measure the temperature difference between upper and lower portions of the associated beam as the carriage traverses the beam. Still other temperature sensors may be positioned to measure the temperature difference between opposite faces of the beam in the X direction as the carriage traverses the beam.

In a preferred embodiment of a scanner beam dynamic deflection measurement system according to the invention, the frame or support structure of the scanner includes parallel upper and lower horizontal beams extending between opposite vertical end support plates and mounting carriages for the opposed gauging heads. Four temperature sensors, such as infrared surface temperature sensors, are mounted in different locations on each carriage, so as to measure the temperatures of upper and lower portions of the associated beam and along opposite faces of the beam. The outputs of the temperature sensors are used to provide temperature differentials providing indications of beam deflection in the Z axis and X axis directions. The temperature differences are continuously updated in dynamic or real time fashion by virtue of the fact that the carriages continue to traverse the lengths of the beams. A linearizing algorithm is applied to the temperature differences in order to perform corrections to the measured parameter values provided by the sensor. The algorithm performs corrections incrementally across the width of the sheet of paper.

Vertical end support plates deflections may also be measured by mounting pairs of temperature sensors on the inner and outer faces of the end support plates. The temperature differences between the inner and outer temperature sensors provide indications of deflections of the end supports.

BRIEF DESCRIPTION OF THE DRAWINGS

Further objects, features and advantages of the present invention can be ascertained by reference to the detailed description, below, in conjunction with the accompanying drawings in which.

DETAILED DESCRIPTION OF THE PREFERRED EMBODIMENTS

Figure 1:
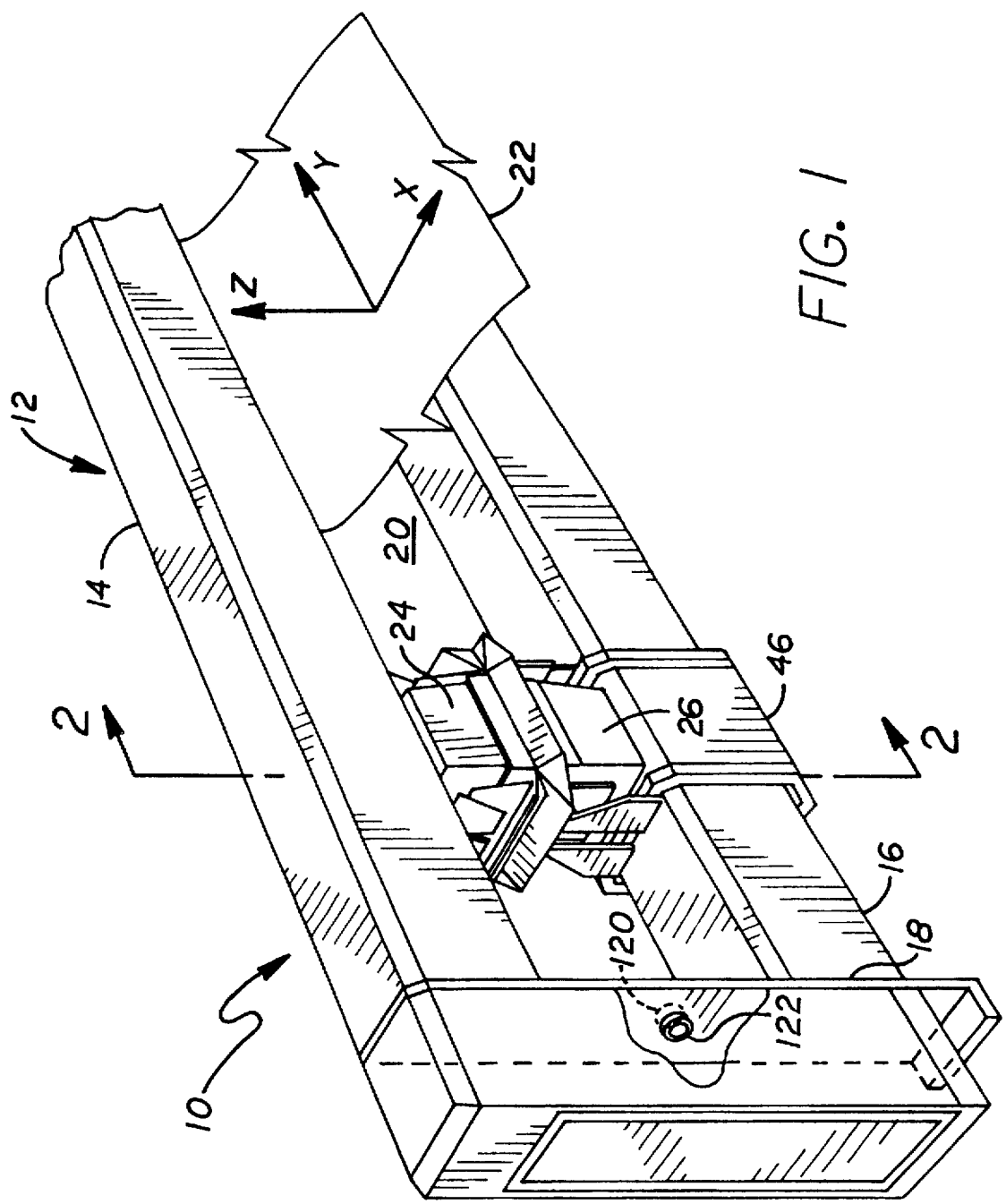
FIG. 1 is a perspective view of a scanner having a dynamic scanner structure deflection measuring system in accordance with the invention.
Figure 2:
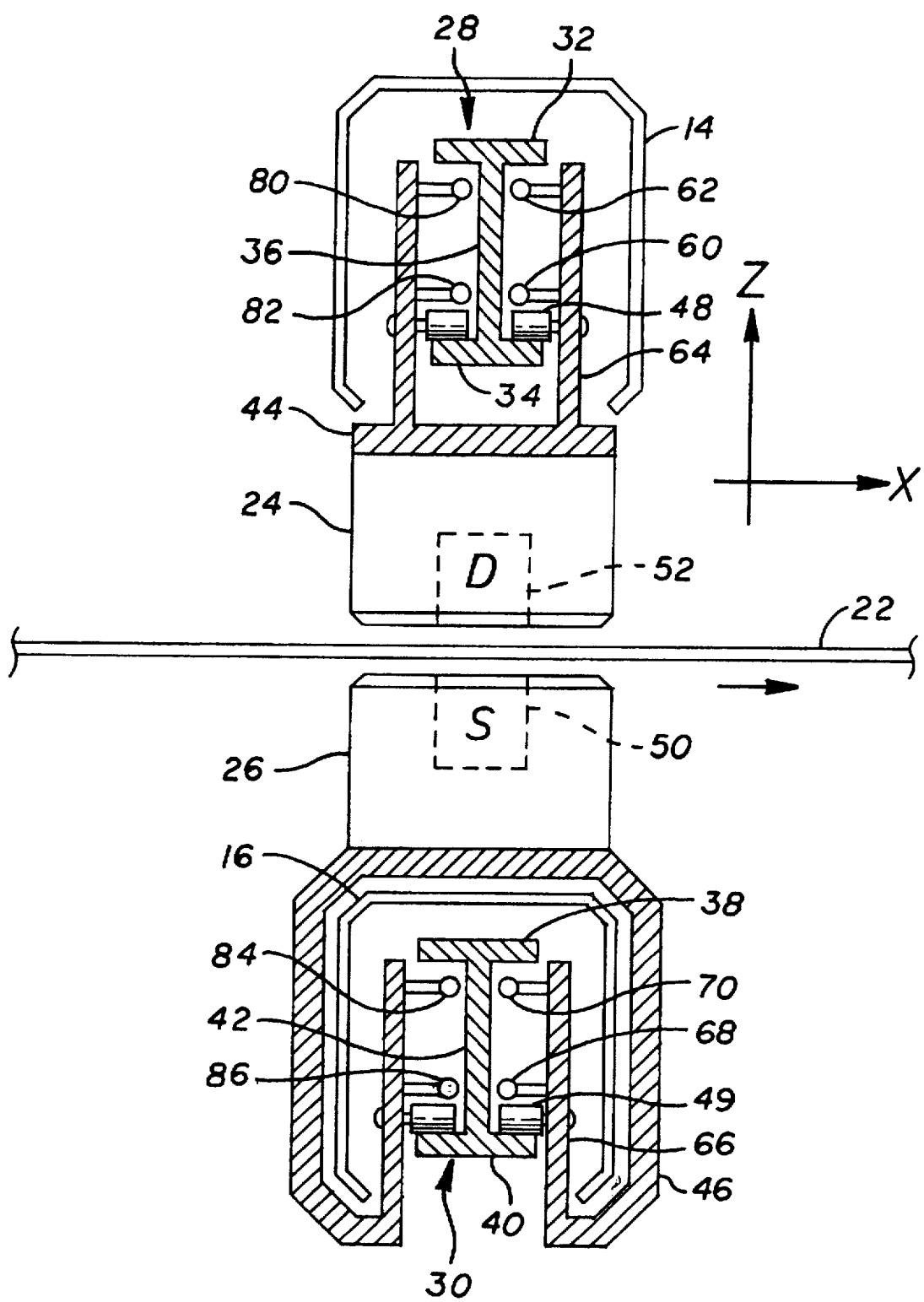
FIG. 2 is a cross section view, in elevation, of the scanner of FIG. 1 as seen along 2—2 in FIG. 1.

FIGS. 1 and 2 show a scanner 10 having a dynamic beam deflection measurement and correction system according to the invention. The scanner 10 includes a rectangular frame 12 which includes elongated, horizontal, upper and lower parallel beam housings 14 and 16 secured to and supported at their opposite ends by a pair of reinforced end support plates 18. The frame 12 defines an opening 20 through which a sheet 22 traveling in the machine direction is continuously advanced through the slot 20. Only a portion of the sheet of paper 22 is shown in FIG. 1, for simplicity of illustration.

As shown in FIG. 1, an XYZ coordinate system provides a reference for the scanner 10. As is well known in the papermaking art, the X axis or direction is the machine direction, the Y axis or direction is the cross direction and the Z axis or direction is the vertical direction.

The scanner 10 includes a gauging head system comprising a pair of gauging heads 24 and 26 disposed on opposite sides of the sheet of paper 22. In the embodiment of FIGS. 1 and 2, the gauging heads 24 and 26 are mounted for cross direction, reciprocating movement along upper and lower I-beams 28 and 30 enclosed within the housings 14 and 16, respectively. The I-beam 28 includes upper and lower horizontal flanges 32 and 34, respectively, and a central vertical web 36. Similarly, the I-beam 30 includes flanges 38 and 40 and a web 42. Motion of the heads 24 and 26 is facilitated by carriages 44 and 46 which carry the heads 24 and 26, respectively. The carriages 44 and 46 are in turn supported by rollers 48 and 49 which ride along the flanges 34 and 40, respectively. Also as well known in the art, the heads 24 and 26 traverse the sheet 22 in unison as the sheet is continuously advanced through the frame opening 20. Consequently, the heads 24 and 26 cover a zig-zag path across the width of the traveling sheet 22. The heads 24 and 26 may be driven by means of conventional design (not shown).

The gauging head system includes a radiation source 50 mounted within the lower head 26 so as to be disposed adjacent the lower surface of the sheet of paper 22. The gauging system also includes a radiation detector 52 mounted within the upper head 24 so as to be disposed adjacent the upper surface of the sheet of paper 22. The radiation source 50 and detector 52 may be of conventional design. For example, the radiation source 50 may emit ionizing radiation which is absorbed to some extent by the sheet of paper 22. The radiation detector 52 produces an electrical signal in response to the amount of radiation received, which, by way of example, may be used to determine the basis weight of the sheet. It will be evident to those skilled in the art that the placement of the radiation source 50 and radiation detector 52 may be reversed, with the source 50 being carried by the upper head 24 and the detector 52 being carried by the lower head 26.

Figure 5:
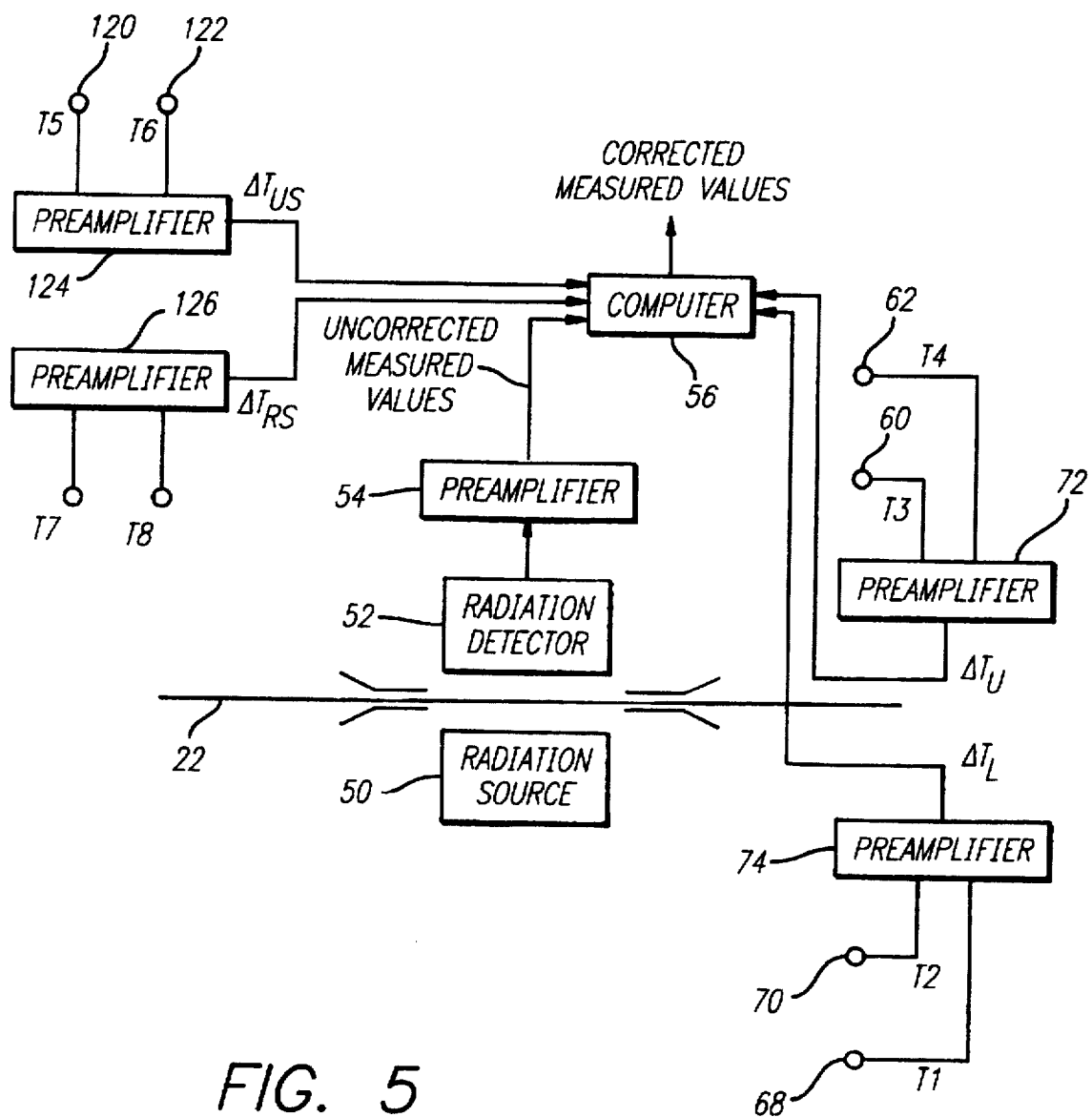
FIG. 5 is a schematic and block diagram illustrating portions of the measurement system which may be used with the scanner of FIG. 1.

As shown in FIG. 5, signals representing measured values from the radiation detector 52 are amplified by a preamplifier 54 before being passed to a computer 56. The measured value provided to the computer 56 will be accurate so long as the Z direction gap separating the radiation source 50 and detector 52 is maintained constant and in alignment in the X and Y directions.

The computer 56 processes information provided thereto such as basis weight and/or other parameters of the sheet of paper 22. As previously described, the computer 56 can be used to operate a control and monitoring system for adjusting various parameters within the papermaking process such as the profile of the slice lip of the head box in a papermaking machine. Adjustments are made so as to maintain parameters such as the basis weight of the paper sheet 22 at the desired value.

It is well known that heat radiating from the newly formed sheet of paper 22, and variations in the ambient temperature surrounding the scanner 10, typically produce temperature gradients and therefore distortion in the structural members of the frame 12. The effect which typically results is illustrated in exaggerated, schematic fashion in FIG. 3. In actual practice, the various structural members may be deflected by only a few thousands of an inch from a perfectly straight configuration, due to the effects of temperature. Nevertheless, such small deflections may be significant because of the sensitivity of the sensors utilized.

Figure 3:
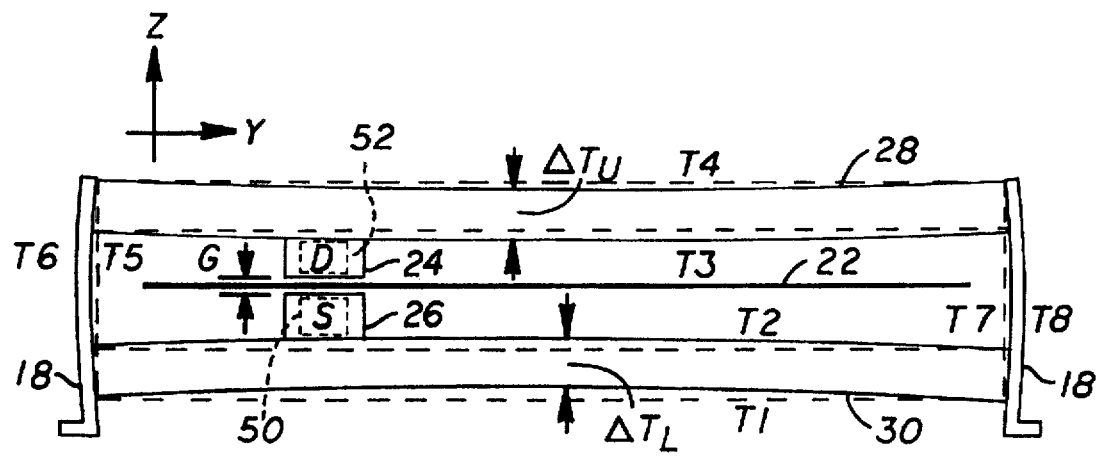
FIGS. 3 and 3A are exaggerated schematics illustrating the thermally induced beam deflections which may occur in the scanner of FIG. 1.

Referring to FIG. 3, the upper beam 28 has a temperature T3 at a lower portion thereof and a temperature T4 at an upper portion thereof. If the temperature T3 is slightly greater than the temperature T4, as is typically the case, then the beam 28 is deflected downwardly, as shown. The difference between the temperatures T3 and T4 may be represented by $\Delta T_U$, where the "U" stands for "upper". Similarly, the lower beam 30 has a temperature T1 at a lower portion thereof and a temperature T2 at an upper portion thereof. If the temperature T2 is slightly greater than the temperature T1, as is typically the case, then the beam 30 is deflected upwardly, as shown. The difference between the temperatures T1 and T2 may be represented by $\Delta T_L$, where the "L" stands for "lower". Because the beams 28 and 30 deflect in the manner shown, the vertical or Z axis gap, designated "G", between the heads 24 and 26 varies as the heads 24 and 26 traverse the width of the sheet of paper 22. In the example shown, at the opposite edges of the sheet of paper 22, the spacing between the heads 24 and 26 is greater than at the center of the sheet of paper 22.

In accordance with the invention, variations in the head-to-head gap G are indirectly determined and used to correct the output of the radiation detector 52. This is done by measuring temperature differentials within the frame structure 12. As shown in FIG. 3, the temperature differences $\Delta T_U$ and $\Delta T_L$ provide information as to the deflection of the upper and lower beams 28 and 30. Moreover, because the temperatures T1, T2, T3, and T4 can vary both at different locations along the lengths of the beams 28 and 30 and with time, it is important that temperature differences such as $\Delta T_U$ and $\Delta T_L$ be determined dynamically, in real time, in accordance with the positions of the heads 24 and 26 along the beams 28 and 30. This is done, in accordance with the invention, by continuously measuring beam temperatures T1, T2, T3, and T4 at locations adjacent the heads 24 and 26, as the heads move along the beams 28 and 30.

As shown in FIG. 3, temperature differences can also cause the end support plates 18 to deflect. Typically, temperature differences between the inner and outer faces of the end supports 18 cause the supports 18 to deflect in the manner shown schematically in FIG. 3. The extent of deflection of the supports 18 can be determined by measuring the temperature difference between the opposite faces thereof. Thus, for example, the temperatures T5 and T6 of the inner and outer faces of the left hand support 18 provide one temperature difference, $\Delta T_{LS}$, where "LS" stands for "left support". In similar fashion, the difference, $\Delta T_{RS}$ (where "RS" stands for "right support"), between temperatures T7 and T8 of the inner and outer faces of the right hand support 18 provide information as to the deflection of the right support 18.

Figure 3A:
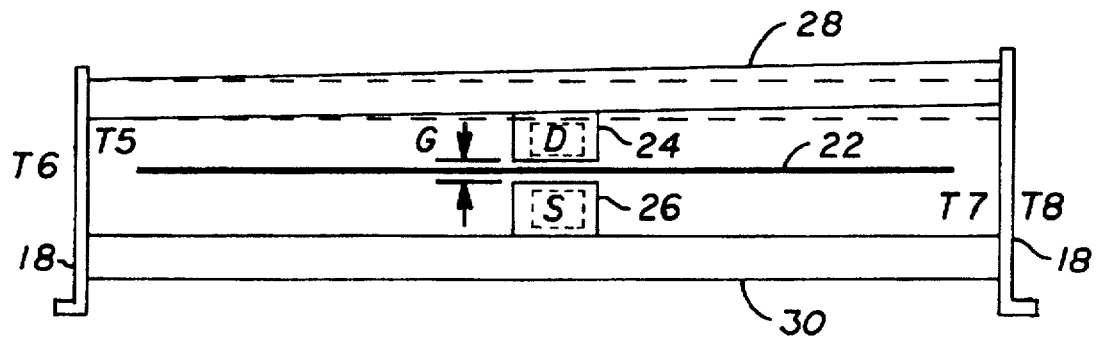

With reference to FIG. 3A, temperature differences between the right and left supports 18 can cause the hotter of these supports (the right support in the example of FIG. 3A) to expand vertically relative to the other support also resulting in Z direction measurement errors due to variations in the head-to-head gap. Temperature sensors T5 and/or T6 and T7 and/or T8 can be used to provide information concerning the relative lengths of the end supports 18 due to thermal effects.

As shown in FIG. 2, the temperatures T1, T2, T3, and T4 are measured using temperature sensors mounted on the carriages 44 and 46. A pair of temperature sensors 60 and 62 are mounted on the carriage 44 so as to be disposed adjacent the lower and upper portions, respectively, of the upper beam 28. Consequently, the temperature sensor 60 measures the temperature T3, and the sensor 62 measures the temperature T4. The temperature sensors 60 and 62 are mounted on a vertical member 64 which forms part of the carriage 44. In similar fashion, a vertical member 66 on the carriage 46 carries temperature sensors 68 and 70. The sensor 68 measures the temperature T1 along the lower portion of the web 42 of the lower beam 30, while the sensor 70 senses the temperature T2 along the upper portion of the web 42. The sensors 68 and 70 can, of course, be positioned to measure the temperatures of the upper and lower beam flanges in addition to, or instead of, the temperature of the beam web.

At any given instant, the sensors 68 and 70 are used to provide the temperature differential $\Delta T_L$ between lower and upper portions of the lower beam 30. Similarly, the sensors 60 and 62 provide the temperature difference $\Delta T_U$ between the lower and upper portions of the upper beam 28. The temperature differences $\Delta T_L$ and $\Delta T_U$ are measured in substantially real time, providing continuously updated temperature gradient information by virtue of the fact that the sensors 60, 62, 68, and 70 are mounted on the carriages 44 and 46, and thereby move along the beams 28 and 30 with the gauging heads 24 and 26.

The temperature sensors 60, 62, 68, and 70 may be infrared surface temperature sensors. An example of a sensor which may be used is the M50 Infracouple infrared temperature sensor manufactured by Mikron Instrument Co., Inc., Wyckoff, N.J., U.S.A.

The manner in which the temperature sensors 60, 62, 68, and 70 are coupled to a computer system to provide corrected measured values is shown in FIG. 5. As shown therein, the sensors 60 and 62 provide the temperatures T3 and T4 to a preamplifier 72. The output of the preamplifier 72 is a function of the temperature differential $\Delta T_U$, and provides it to the computer 56. In similar fashion, the temperature sensors 68 and 70 provide the temperatures T1 and T2 to a preamplifier 74. The preamplifier 74 determines the temperature differential $\Delta T_L$, and provides such temperature differential to the computer 56.

In accordance with the invention, the computer 56 continuously corrects the uncorrected measured values at the output of the preamplifier 54 in accordance with the temperature differentials measured within the support structure 12 such as the temperature differentials $\Delta T_L$ and $\Delta T_U$. This is accomplished by applying well known linearizing algorithms to the output of the radiation detector 52.

Figure 4:
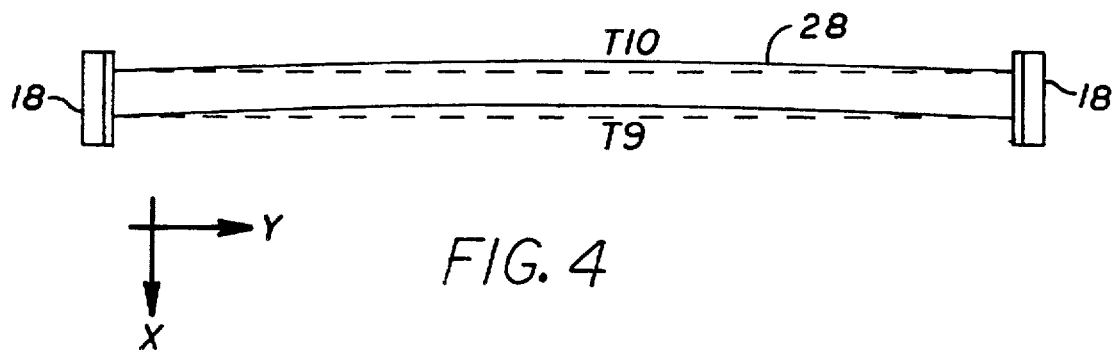
FIG. 4 is a perspective view of one of the beams of the sensor of FIG. 1, illustrating lateral deflection which can occur in the X axis direction due to temperature gradients.

The temperature differentials $\Delta T_L$ and $\Delta T_U$ provide information with respect to beam deflection in the vertical or Z axis direction. As previously noted, variations in the head gap, G, in the vertical or Z axis direction must be detected and compensated for if the scanner 10 is to provide accurate measurements of parameters such as basis weight. However, in accordance with the invention, compensation for thermal beam distortion can also be provided in other directions such as in the X axis or machine direction. This is illustrated in FIG. 4, which shows the upper beam 28 deflected in the X direction. Similar considerations apply with respect to the lower beam 30. As shown in FIG. 4, the beam 28 has a temperature T9 on one side thereof and a temperature T10 on the opposite side thereof. Differences between the temperatures T9 and T10 can produce lateral deflection of the beam 28 in the X axis direction, as illustrated by the solid lines in FIG. 4. Beam deflections in the X axis direction can cause misalignments between the source 50 and detector 52 relative to each other, thereby introducing yet another possibility of error in the readings provided by the scanner 10. To correct for this, temperature sensors 80 and 82 can be mounted on the upper carriage 44 which, in conjunction with the temperature sensors 60 and 62, respectively, can measure temperature differentials providing an indication of X direction deflections of the upper beam 28. Similarly, temperature sensors 84 and 86 can be mounted on the lower head carriage 46 so as to provide, in cooperation with temperature sensors 70 and 68, X direction temperature differences across the beam 30.

Figure 6:
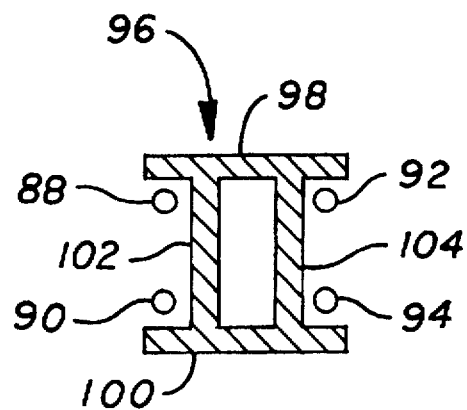
FIG. 6 is a transverse cross section view of a scanner beam of dual I-beam configuration, showing a preferred placement of temperature sensors in relation thereto.
Figure 7:
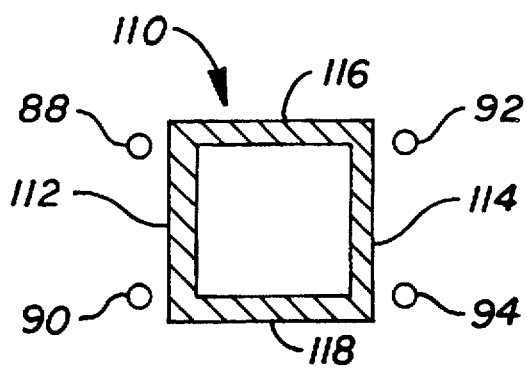
FIG. 7 is a transverse cross section view of a scanner beam of box beam configuration, showing one placement of temperature sensors in relation thereto.
Figure 8:
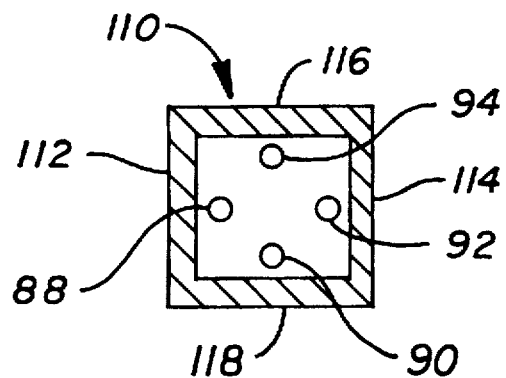
FIG. 8 is a transverse cross section view of another scanner beam of box beam configuration, showing an alternative placement of temperature sensors in relation thereto.

FIGS. 6–8 show preferred temperature sensor placements for two additional beam cross section configurations. As before, the temperature sensors are mounted on carriages which move along upper and lower beams. In FIGS. 6–8, however, the carriages have been omitted for simplicity of illustration.

FIG. 6 shows the preferred placement of four temperature sensors 88, 90, 92, and 94 in the case of a beam 96 of dual I-beam cross section. The beam 96 has upper and lower flanges 98 and 100, and a pair of generally vertical, spaced-apart intermediate webs 102 and 104 connecting the flanges. The temperature sensors 88 and 90 are mounted on the associated carriage (not shown) so as to be disposed on the outside of the web 102 adjacent the upper flange 98 and the lower flange 100, respectively. Similarly, the temperature sensors 92 and 94 are positioned on the outside of the other web 104 below the upper flange 98 and above the lower flange 100, respectively. By positioning the temperature sensors in this fashion, temperature differentials in both the Z and X directions across the beam 96 can be measured.

FIGS. 7 and 8 show a beam 110 having a square or rectangular box cross section. The beam 110 includes side walls 112 and 114 and top and bottom walls 116 and 118. In the example of FIG. 7, the temperature sensors 88, 90, 92, and 94 are mounted on the associated carriages proximate the four external corners of the box beam 110. In FIG. 8, the temperature sensors 88, 90, 92, and 94 are mounted to sense internal wall surface temperatures. In either case, by positioning the temperature sensors as shown, temperature differentials in both the Z and X directions across the beam 110 may be determined.

In accordance with another aspect of the present invention, Y direction deflections of the vertical end supports 18 may also be measured and used to correct the output of the radiation detector 52. As previously described in connection with FIG. 3, the left hand support 18 has inner and outer surface temperatures T5 and T6 while the right hand end support 18 has inner and outer surface temperatures T7 and T8, respectively. These temperatures are measured by temperature sensors mounted on or otherwise associated the faces of the supports 18. For example, temperature sensors 120 and 122 (FIG. 1) associated with the left support 18 measure temperatures T5 and T6, respectively. With reference again to FIG. 5 as before, the electrical output signals from preamplifier circuits 124 and 126 representing the differences, $\Delta T_{LS}$ between the temperatures T5 and T6 and the temperatures T7 and T8, respectively are processed by the computer 56 to correct the uncorrected measured values for deflections in the end support plates 18.

While various forms and modifications of the invention have been suggested, it will be appreciated that the invention is not limited thereto but encompasses all expedients and variations falling within the scope of the appended claims.

What is claimed is:

1. A process for measuring the values of a parameter of a sheet of material by a sensor system including first and second head members movably mounted by a support structure on opposite sides of the sheet of material and for correcting the measured values of the parameter to account for variability of the separation of the first and second head members, comprising the steps of:

measuring the values of the parameter with the sensor system without correction for variability of the separation of the first and second head members from one another to provide uncorrected, measured values;

determining variability of the separation of the first and second head members by measuring a temperature differential between at least two different locations in the support structure; and correcting the uncorrected measured values according to the determined variability of the separation of the first and second head members.

2. A process according to claim 1, wherein the support structure includes upper and lower beams mounting the first and second head members for movement therealong, and the step of determining variability includes sensing temperatures at upper and lower portions of each of the upper and lower beams to determine temperature differentials therebetween.

3. A process according to claim 2, wherein the sensing of temperatures at the upper and lower portions of each of the upper and lower beams is generally continuously performed adjacent the locations of the first and second head members as the first and second head members move along the upper and lower beams.

4. A process according to claim 1, wherein the support structure includes upper and lower beams mounting the first and second head members for movement therealong, and the step of determining variability includes sensing temperatures at opposite sides of each of the upper and lower beams to determine temperature differentials therebetween.

5. A process according to claim 1, wherein the support structure includes upper and lower beams mounting the first and second head members for movement therealong and end supports disposed between the upper and lower beams, and the step of determining variability includes sensing temperatures at inner and outer portions of each of the end supports to determine temperature differentials therebetween.

6. A process according to claim 1, wherein the support structure includes upper and lower beams mounting the first and second head members for movement therealong, and the step of determining variability includes generally continuously sensing temperatures at upper and lower portions of each of the upper and lower beams and at opposite sides of each of the upper and lower beams adjacent the locations of the first and second head members to determine temperature differentials therebetween as the first and second head members move along the upper and lower beams.

7. A process according to claim 6, wherein the step of correcting the uncorrected measured values includes applying a linearizing algorithm to the temperature differentials to preform corrections incrementally across the width of the sheet of material.

8. Apparatus for measuring the values of a parameter of a sheet of material, comprising the combination of:
first and second head members movably mounted by a support structure on opposite sides of the sheet of material for measuring the values of the parameter;
means for measuring a temperature differential between at least two different locations in the support structure; and
means for correcting the measured values of the parameter in accordance with the measured temperature differential.

9. Apparatus in accordance with claim 8, wherein the means for measuring a temperature differential includes at least two infrared temperature sensors at the at least two different locations.

10. Apparatus in accordance with claim 8, wherein the support structure includes upper and lower beams for movably mounting the first and second head members, and the means for measuring a temperature differential includes means for measuring an upper beam temperature differential between upper and lower locations on the upper beam and means for measuring a lower beam temperature differential between upper and lower locations on the lower beam.

11. Apparatus in accordance with claim 8, wherein the support structure includes upper and lower beams for movably mounting the first and second head members, and the means for measuring a temperature differential includes means for measuring an upper beam temperature differential between opposite sides of the upper beam and means for measuring a lower beam temperature differential between opposite sides of the lower beam.

12. Apparatus in accordance with claim 8, wherein the support structure includes upper and lower beams, the first head member is mounted for movement along the upper beam by a first carriage, the second head member is mounted for movement along the lower beam by a second carriage, and the means for measuring a temperature differential includes a first plurality of temperature sensors mounted in spaced-apart locations on the first carriage and a second plurality of temperature sensors mounted in spaced-apart locations on the second carriage.

13. Apparatus in accordance with claim 12, wherein each of the first and second pluralities of temperature sensors includes upper and lower temperature sensors for determining a temperature differential between upper and lower portions of an associated one of the upper and lower beams.

14. Apparatus in accordance with claim 12, wherein each of the first and second pluralities of temperature sensors includes opposite side temperature sensors for determining a temperature differential between opposite side portions of an associated one of the upper and lower beams.

15. Apparatus in accordance with claim 12, wherein the support structure includes end supports extending between the upper and lower beams, and the means for measuring a temperature differential includes pairs of temperature sensors mounted on opposite sides of each of the opposite end supports.

16. A scanner beam dynamic deflection measurement system for use with a sheet material scanner having opposite first and second heads mounted by first and second carriages for movement along upper and lower beams, the system comprising:
first and second pluralities of temperature sensors mounted in spaced-apart locations on the first and second carriages;
means coupled to the first and second pluralities of temperature sensors for determining temperature differentials therebetween; and
means responsive to the determined temperature differentials for providing a correction signal compensating for temperature caused deflections of the upper and lower beams.

17. A scanner beam dynamic deflection measurement system in accordance with claim 16, wherein each of the first and second pluralities of temperature sensors includes upper and lower sensors for sensing temperatures at upper and lower portions of an associated one of the upper and lower beams as the first and second carriages move the first and second heads along the upper and lower beams.

18. A scanner beam dynamic deflection measurement system in accordance with claim 16, wherein each of the first and second pluralities of temperature sensors includes opposite side sensors for sensing temperatures at opposite side portions of an associated one of the upper and lower beams as the first and second carriages move the first and second heads along the upper and lower beams.

19. A scanner beam dynamic deflection measurement system in accordance with claim 16, wherein the scanner has opposite end supports extending between the upper and lower beams at opposite ends thereof, and further including pairs of temperature sensors mounted on opposite faces of the end supports, means coupled to the pairs of temperature sensors for determining temperature differentials therebetween, and means responsive to the determined temperature differentials for providing a correction signal compensating for temperature-caused deflections of the opposite end supports.

20. A scanner beam dynamic deflection measurement system in accordance with claim 16, wherein each of the first and second pluralities of temperature sensors comprises four temperature sensors arranged to detect temperature differences between upper and lower portions and between opposite side portions of an associated one of the upper and lower beams.

21. A scanner beam dynamic deflection measurement system in accordance with claim 20, wherein each of the upper and lower beams is of I-beam cross-sectional configuration and the four temperature sensors of an associated one of the first and second pluralities of temperature sensors include a first pair of temperature sensors positioned on opposite sides of a center portion of the beam adjacent a top end thereof and a second pair of temperature sensors positioned on opposite sides of the center portion of the beam adjacent a bottom end thereof.

22. A scanner beam dynamic deflection measurement system in accordance with claim 20, wherein each of the upper and lower beams is of dual I-beam cross-sectional configuration and the four temperature sensors of an associated one of the first and second pluralities of temperature sensors include a first pair of temperature sensors positioned on opposite sides of dual vertical I-beam portions of the beam adjacent a top end thereof and a second pair of temperature sensors positioned on opposite sides of dual vertical I-beam portions of the beam adjacent a bottom end thereof.

23. A scanner beam dynamic deflection measurement system in accordance with claim 20, wherein each of the upper and lower beams is of box beam cross-sectional configuration so as to define four corners, and each of the four temperature sensors of an associated one of the first and second pluralities of temperature sensors is disposed adjacent a different one of the four corners of the beam.

* * * * *